United States Patent [19]

García et al.

[11] Patent Number: 5,786,377
[45] Date of Patent: Jul. 28, 1998

[54] PYRROLO[3,2-E]INDOL DERIVATIVES, PROCESS FOR THE PREPARATION THEREOF AND APPLICATIONS

[75] Inventors: José Delamano García, Villagarcía de Arosa; Gabriel Tojo Suarez, Santiago de Compostela; Carmen López Goti, Nede; Jesús Fernández Almeida, Zamora; Dolores García Gravalos, Madrid, all of Spain; Glynn Thomas Faircloth, Cambridge, Mass.

[73] Assignee: Universidad de Santiago de Compostela, LaCoruna, Spain

[21] Appl. No.: 790,904

[22] Filed: Jan. 29, 1997

Related U.S. Application Data

[63] Continuation of Ser. No. 491,870, filed as PCT/ES94/00122 Nov. 18, 1994.

[30] Foreign Application Priority Data

Nov. 19, 1993 [ES] Spain ........................ 9302430

[51] Int. Cl.$^6$ ........................ A61K 31/40; C07D 487/04
[52] U.S. Cl. ........................ 514/410; 514/411; 548/421; 548/433
[58] Field of Search ........................ 548/421, 433; 514/410, 411

[56] References Cited

U.S. PATENT DOCUMENTS

5,070,092  12/1991  Kanda et al. ........................ 548/421 X

FOREIGN PATENT DOCUMENTS

| 0359454-A | 3/1990 | European Pat. Off. |
| 406749 | 1/1991 | European Pat. Off. |
| 8-034789 | 2/1996 | Japan. |
| 9116324-A | 10/1991 | WIPO. |

*Primary Examiner*—Fiona T. Powers
*Attorney, Agent, or Firm*—Klauber & Jackson

[57] ABSTRACT

The pyrrolo[3,2-e] derivatives of the present invention have the formulae (I), (Ia) and (II) wherein R is substituted or unsubstituted aryl or heteroaryl, R' is substituted or unsubstituted alkanoyl, alkenoyl, alkynoyl, arenocarbonyl or heteroarenocarbonyl and X is chloro, bromo, iodo or alkylsulfonyl or arylsulfonyl. The compounds find utility as agents having antitumor activity, and are thus useful agents in the treatment of cancer.

16 Claims, No Drawings

PYRROLO[3,2-E]INDOL DERIVATIVES, PROCESS FOR THE PREPARATION THEREOF AND APPLICATIONS

This application is a Continuation of application Ser. No. 08/491,870, filed May 15, 1996 now pending, which is a 371 of PCT/ES94/00122 filed Nov. 18, 1994.

TECHNICAL FIELD OF THE INVENTION

The present invention fits in the technical field of antitumoral agents, that have in their structure a pyrroloindol group.

More particularly, the present invention provides new-pyrrolo[3,2-e]indol derivatives which have a high antitumoral activity together with a lower toxicity with regard to known compounds.

PRIOR ART OF THE INVENTION

D. L. Boger et al. (J. Am. Chem. Soc., 113, 2779 (1991) showed that the structural unity of cyclopropa c indol-4-one is responsible for the antitumoral activity of the agent CC-1065 of formula (1):

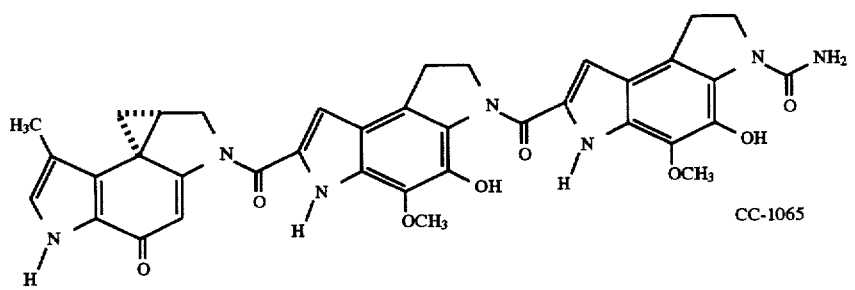

This compound is an extremely strong cytoxine whose biological action is attributed basically to its capacity to covalently bond with structure of the DNA helix ((1) Chidester, C. G.; Krueger, W. C.; Mizsak, S. A.; Duchamp, D. J., Martin, D. G. J. Am. Chem. Soc. 1981, 103, 7629 and references therein. (2) Li, L. H.; Swenson, D. H.; Schpok, S. L.; Kuentzel, S. L.; Dayton, B. D.; Krueger, W. C. Cancer Res. 1982, 42, 999. (3) Swenson, D. H.; Li, L. H.; Hurley, L. H.; Rokem, J. S.; Petzold, G. L.; Dayton, B. D. Wallace, T. L.; Lin, A. H., Krueger, W. C. Cancer Res. 1982, 42, 2821.

(4) Bhuyan, B. K.; Newell, K. A.; Crampton, S. L.; von Hoff, D. D. Cancer Res. 1982, 42, 3532. (5) Hurley, L. H.; Reynolds, V. L.; Swenson, D. H.; Petzhold, G. L.; Scahill, T. A. Science (Washington, D.C.) 1984, 226, 843. (6) Reynolds, V. L.; Molineux, L. J., Kaplan, D. J.; Swenson, D. H.; Hurley, L. H. Biochemistry 1985, 24, 6228. (7) Reynolds, V. L.; McGroven, J. P.; Hurley, L. H. J. Antibiot. 1986, 39, 319.)

However, though the compound CC-1065 was, at the beginning, chosen for its development as an anticarcinogenic agent by the NCI (8) Ducros, J.; Suffness, M.; Cancer Treat. Rev. 1981, 8, 63), said development was interrupted due to its high toxicity, producing delayed deaths in mice at therapeutic doses (9) McGovern, J. P.; Clarke, G. L.; Pratt, E. A.; DeKoning, T. F.; J. Antibiot. 1984, 37, 63.)

Therefore, scientific research has been directed towards finding more or less important modifications of the structural formula of CC-1065 that, maintaining its anticarcinogenic capacity, considerably reduced the side effects.

In these lines Adocelesine of formula (2):

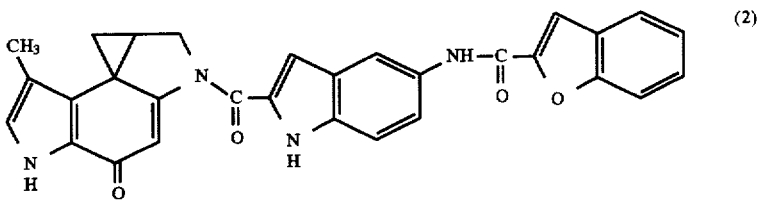

has been synthesized, which not only maintains the high strength of (1) but that also greatly exceeds the natural product in tumoral effectiveness, without provoking delayed lethality ((10) Werpehoski, M. A.. Tetrahedron Letter. 1986, 4103.)

Presently Adolecesine is in phase III of clinical studies ((11) Li, L. H. et al. Investigational New Drugs 9, 137–148, 1991; (12) Smith, K. S. et al., Cancer Cheamater. Pharmacol. 30: 348–354, 1992.)

Another compound of interest that, though the studies thereon are not as advanced as those on Adocelesine, but that is very promising is Carcelesine, of formula:

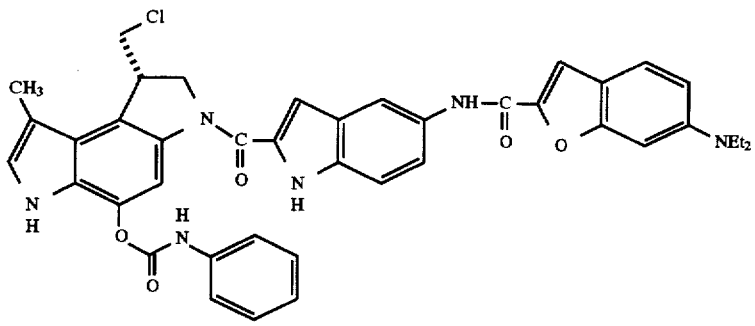

((13) Li, L. H. et al., Cancer Research, 52, 4904–4913, 1992)

Another compound to be pointed out is CBI-Ind$_2$, of formula:

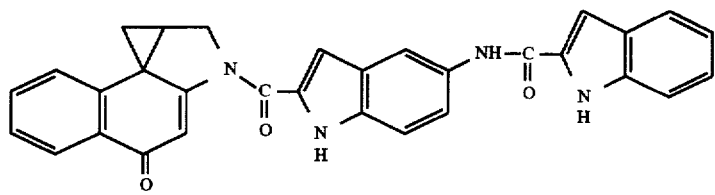

prepared by Boger ((14) Boger, D. L. et al., Bioorganic and Medicinal Chemistry Letters, 1:115–120, 1991) that shows very good results in the P388 model in vivo.

Likewise, the compounds of formula (5)

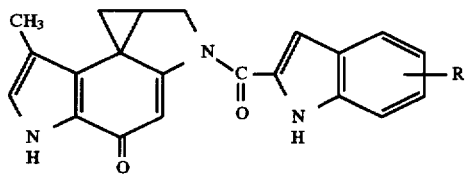

have been obtained, wherein R can have the following meanings:

5-OMe
6-OH, 7-Ome
5-NHCONH[2]
5-NHCOPh
5-NHCO-2-indolyl
5-NHCO-5-(NHCONH$_2$)-2-indolyl
54-NHCO-5-(NHCOPh)-2-indolyl with acceptable anticarcinogenic activity indexes with regard to toxicity ((15) M. A. Warpehoski et al. J. Med. Chem, 1988, Vol. 31, No. 3).

However, it is still necessary to advance in the search for compounds structurally related to those cited in the above paragraphs, with a view of introducing other modifications that improve even more the anticarcinogenic/toxicity relationship. In this context, the present invention provides some new pyrrolo[3,2-]indol derivatives that optimize said relationship.

DETAILED DESCRIPTION OF THE INVENTION

The present invention, just as it is indicated in its title, refers to new pyrrolo[3,2-e]indol derivatives with anticarcinogenic activity, to the processes for the preparation thereof and to its applications.

The new pyrrolo[3,2-e]indol derivatives of the present invention are characterized in that they have the following formulae (I), (Ia) and (II):

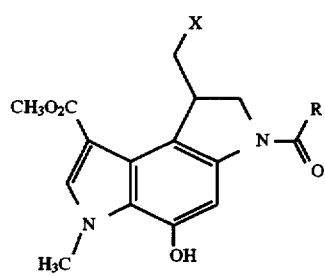

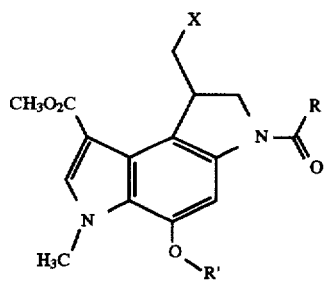

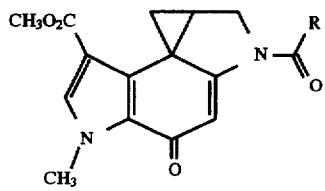

wherein R represents an aryl group (such as benzyl, naphthyl or phenanthryl) or heteroayl (such as indolyl), all of them substituted or not substituted; R' represents an alkanoyl, alkenoyl, alkynoyl, areocarbonyl or heteroarenocarbonyl group substituted or not substituted and X represents chlorine, bromine, iodine or alkyl or arylsulfonyloxy.

The preferred meanings for R are indolyl or indolyl substituted especially by an aryl or heteroarylcarbonylamino group.

The compounds especially preferred of the present invention correspond to the following formula (III) to (VI):
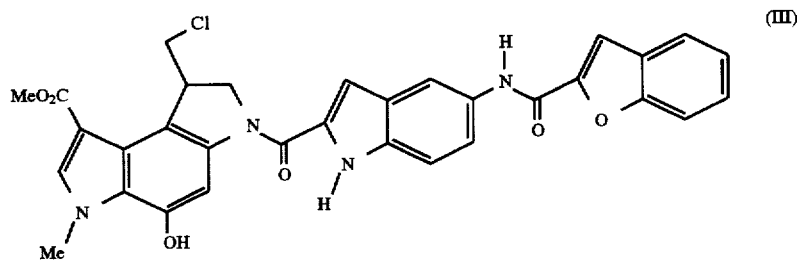
(III)
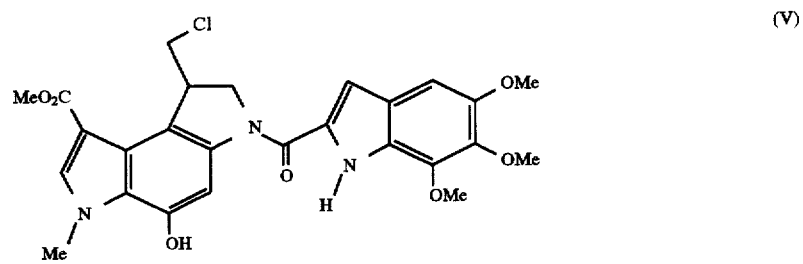
(V)
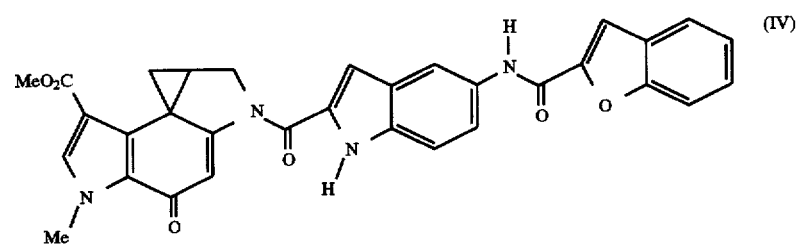
(IV)
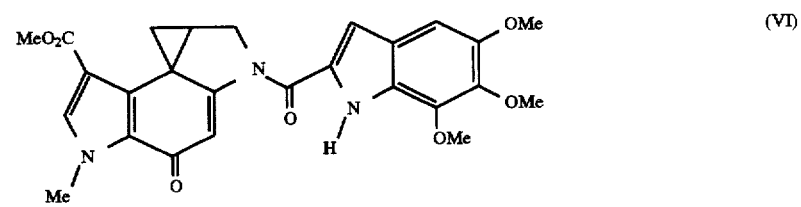
(VI)
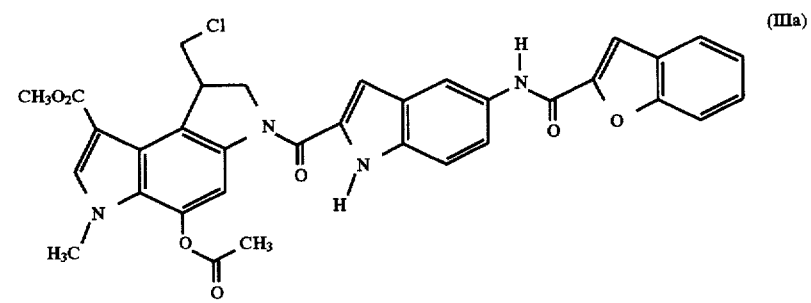
(IIIa)
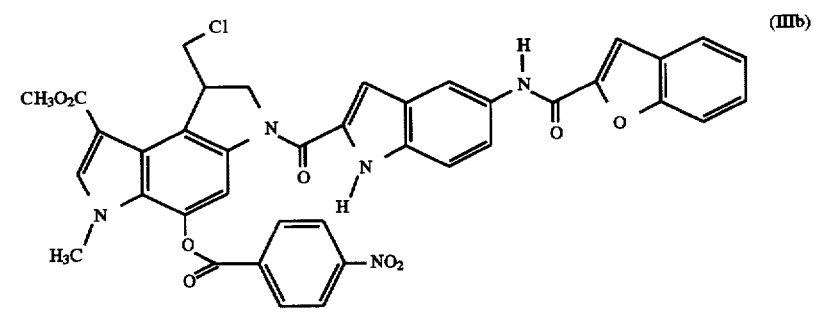
(IIIb)

The compounds of formula (I), (Ia) and (II) of the present invention, are obtained from the compound of formula (VII):

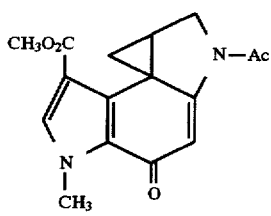

(VII)

wherein Ac represents an acyl group, generally, acetyl. In a first phase, the compound of formula (VII) is deacylated to produce the compound of formula (VIII):

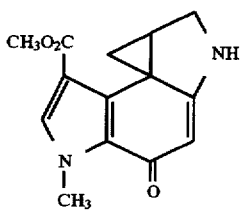

(VIII)

The deacylation reaction is carried out in a basic medium and in a suitable organic solvent. Normally, the base used is an alkoxide, preferably, sodium methoxide and the organic solvent is methanol.

In a second phase, the compound (VIII) is subjected to a reaction to open the cyclopropyl ring to produce a compound of formula (IX):

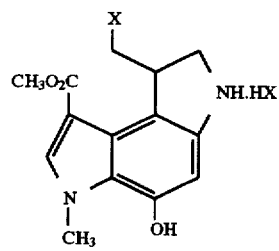

(IX)

wherein X has the meaning given above for the formula (i.)

The reaction of opening the cyclopropyl ring is carried out by reacting the compound (VIII) with an acid in an organic solvent. Among the acids used, one can mention hydrogen chloride, hydrogen bromide and hydrogen iodide as well as the aryl or alkylsulfonic acid thereof. As the preferred organic solvent ethyl acetate can be mentioned.

In a third phase, the compound of formula IX thus obtained is condensed with an acid of formula

 R—COOH (X)

wherein R has the meaning given above, or a reactive derivative of the same to produce the active compound of formula (I) indicated above. Condensation is carried out in an organic solvent and in the presence of a condensing agent.

This reaction can be carried out in a carboxylic areno acid (such as benzoic, naphthoic, phenanthroic acid) or a carboxylic geneteroarene acid (such as indolcarboxylic acid) all of them substituted or not substituted.

As an organic solvent to carry out this reaction amides, in particular, N,N-dimethylformamide or N,N-dimethylacetamide, are preferred. As a condensing agent carbodiimides are preferred.

The active compounds of formula (II) indicated above can be obtained from the active compounds of formula (I) in a fourth phase of the process that comprises treating said compounds of formula (I) with a base in a suitable solvent.

The preferred bases to carry out this transformation are amines and, especially, tirethylamine.

As a solvent, a mixture of water with an organic solvent, preferably a mixture of water and acetonitrile, is preferably used.

The active compounds of formula (Ia) can be obtained from the active compounds of formula (I) in a fifth phase of the process that comprises treating said compounds of formula (I) with, alternatively; (a) a carboxylic acid in the presence of a condensing agent; or else, (b) a carboxylic acid chloride in the presence of a base; both alternatives in a suitable solvent.

In alternative (a) an alkanoic, areno or heteroarenocarboxylic acid substituted or not substituted can be used. As a condensing agent and a solvent those indicated in the transformation of compound (IX) into compound (I) are preferred.

In alternative (b) al alkanoic, areno or heteroarenocarboxylic acid chloride substituted or not substituted can be used. As a base the use of an amine, preferably triethylamine, is preferred. As a solvent an organic solvent, preferably tetrahydrofuran is used.

The compound of formula (VII), used as a starting product for the process of the present invention, can be obtained in turn from the compound of formula (XI):

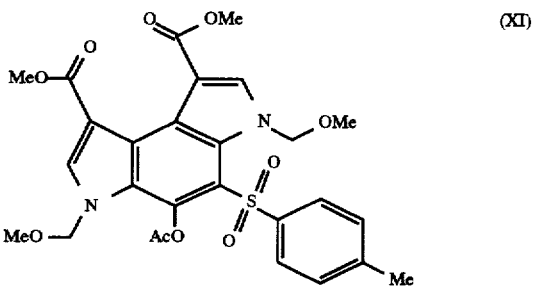

(XI)

which is one of the products of Spanish patent no. 9201894 of the same applicant, by a method already described also by the same applicant, but that is summarized in the following paragraphs as a reference.

In a first stage, one of the methoxymethyl groups of compound (XI) is eliminated, by treating it with formic acid at room temperature, to product the compound of formula (XII):

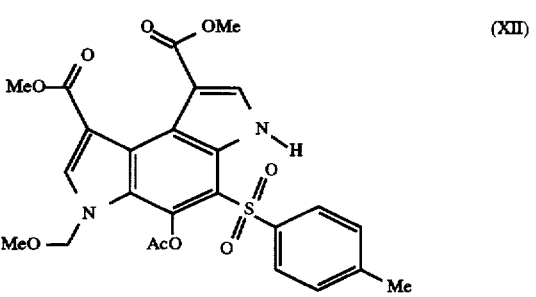

(XII)

In a second stage, the selective reduction of one of the pyrrolic rings by treating (XII) with Et₃SiH in trifluoroacetic acid is carried out, followed by treatment with aceitc anhydride in pyridine to produce a mixture of compounds of formula (XIII) to (XIV):

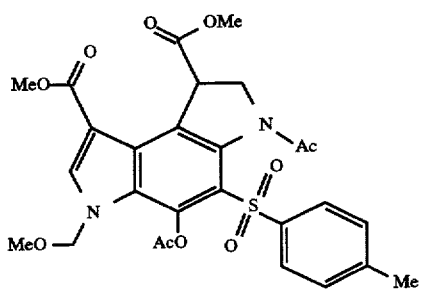

(XIII)

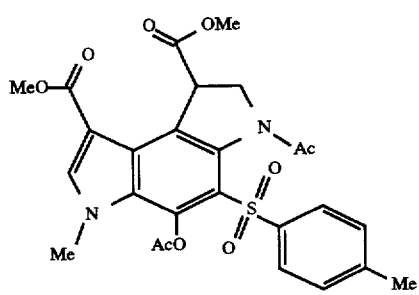

(XIV)

In a third stage, the mixture of (XIII) and (XIV) is subjected to a reaction to eliminate the sulfone group by treating the same with sodium and naphthalene in tetrahydrofuran followed by treatment with an acetic anhydride in pyridine, to give a mixture of compounds of formula (XV) and (XVI):

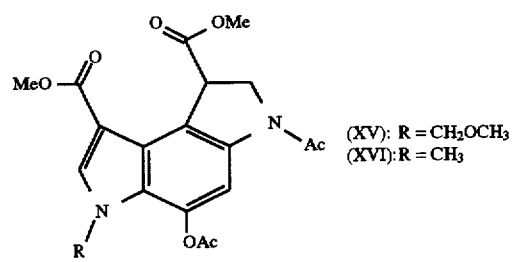

(XV): R = CH₂OCH₃
(XVI): R = CH₃

In a fourth stage, the compound of formula (XVI), preferably separated from the mixture, is subjected to a selective reduction of aliphatic ester or O-deacetylation, by reaction with LiAlH₄ in tetrahydrofuran, to produce the compound of formula (XVII):

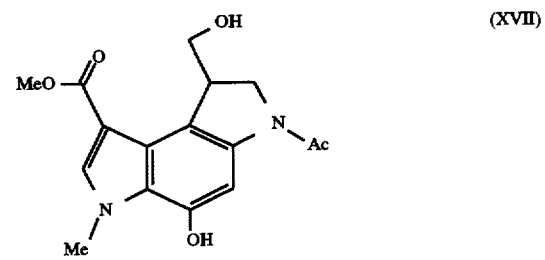

(XVII)

In a fifth stage, the compound (XVII) is subjected to Mitsunobu reaction ((12) O. Mitsunobu, Synthesis 1981, 1) to produce the desired compound of formula (VII).

The compounds of formulae (I) and (II) of the present invention and especially, the compounds of formulae (III), (IV), (V) and (VI) are characterized in that they have a high anticarcinogenic activity in vivo together with a very low toxicity, as is manifested in the biological activity studies that will be cited hereinafter. This makes them especially ideal for used as agents for the therapeutic treatment of cancer in its diverse manifestations and, especially, in cases of leukemia.

EMBODIMENTS OF THE INVENTION

The present invention is additionally illustrated by means of the following Examples that do not limit its scope, which is defined solely and exclusively by the attached set of claims.

PREPARATION EXAMPLE

Synthesis of methyl 6-acetyl-8-hydroxymethyl-4-ol-3-methyl-3,6,7,8-tetrahydropyrrolo[3,2-]indol-1-carboxylate 1. Synthesis of dimethyl 4-acetoxy-3-methoxymethyl-5-tosyl-3,6-dihydropyrrolo[3,2-e]indol-1,8-dicarboxylate (XII):

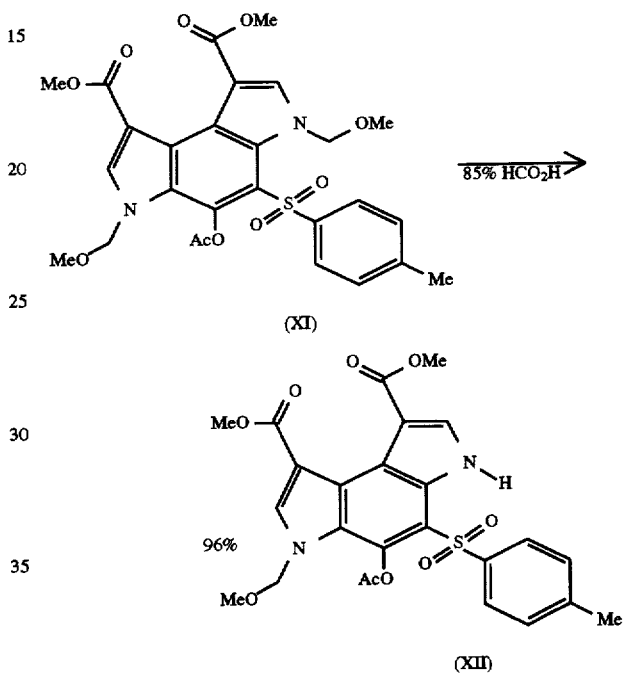

1831 mg of pyrroloindol (XI) (3.20 mmol) were dissolved in 30 mL formic acid 85%, maintaining agitation at room temperature for 24 hours.

To elaborate water (250 mL) was added, extraction was carried out with CH₂Cl₂ (3×75 mL) and the organic phase was dried with anhdrous NaSO₄. Finally, the residue obtained upon evaporating the solvent was purified by chromatography in a silica flash gel column (16×2 cm φ, hexane:EtOAc gradient from 50 to 60% EtOAc), allowing to obtain after vacuum drying, 1623 mg (96%) of the mono-unprotected compound (XII.) m.p.: 135°–137° C. (EtOAc:hexane). Rf.: 0.52 (CH₂Cl₂:EtOAc 17:3) IR (NaCl, $\gamma_{max}$): 1725, 1790, 2950, 3410 cm⁻¹ UV (Ethanol, $\lambda_{max}$) 206, 242, 268, 328 nm ¹H—NMR(CDCl₃): 2.33 (s, 3H, ArOCOCH₃), 2.42 (s, 3H, ArCH₃), 3.18 (s, ArCH₂OCH₃), 3.81 (s, 3H, ArCO₂CH₃), 3.82 (s, 3H, ArCO₂CH₃), 5.02 (d, 1H, J=10.8 Hz, ArCH₂OCH₃), 5.87 (d, 1H, J=10.8 Hz, ArCH₂OCH₃), 7.21 (d, 2H, J=8.3 Hz, ArH), 7.78 (d, 2H, J=8.2 Hz, ArH), 7.79 (s, 1H, ArH), 7.92 (d, 1H, J=2.9 Hz, ArH), 10.68 (s wide, 1H, ArNH). ¹³C—NMR(CDCl₃): 21.4, 21.45, 51.3, 51.4, 55.3, 80.3, 111.2, 111.5, 113.0, 116.8, 125.3, 125.8, 126.5, 129.1, 129.8, 130.6, 134.5, 137.4, 139.7, 144.7, 165.4, 165.8, 169.2 Mass spectrum (m/e, %): 528 (M⁺, 4), 497 (M⁺—CH₃O5), 486 (M⁺CH₂CO, 100), 454 (M⁺CH₂CO—CH₃OH, 58), 331 (M⁺—CH₂CO—CH₃ (C₆H₄)SO₂·7), 299 (M⁺—CH₂CO—CH₃(C₆H₄)SO₂—CH₃OH, 3), 139 (CH₃(C₆H₄)SO⁻, 13) 91 (CH₃(C₆H₄)⁻, 2. Reduction of dimethyl 4-acetoxy-3-methoxymethyl-5-tosyl-3,6-dihydropyrrolo[3,2-e]indol-1,8-dicarboxylate (XII) with Et$_3$SiH in an acid medium.

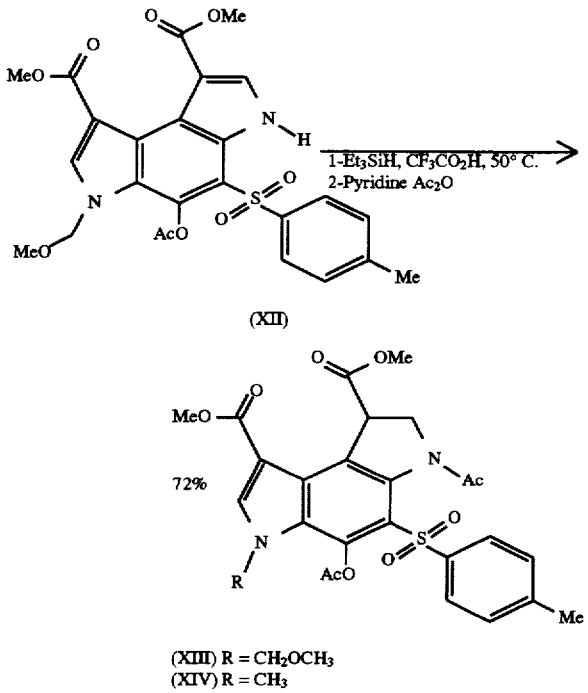

(XIII) R = CH$_2$OCH$_3$
(XIV) R = CH$_3$ 4.5 ml of trifluoroacetic acid (58.41 mmol) was added to a mixture of the pyrroloindol (XII) (500 mg. 0.946 mmol) and Et$_3$SiH (0.9 mL, 5.65 mmol) under argon, heating the resulting mixture in a paraffin bath at 60° C. for 8 hours. Then, the mixture was cooled in a bath at −50° C. and 9 mL of pyridine (115 mmol), 3 ml of acetic anhydride (31.73 mmol) and 3 mL of CH$_2$Cl$_2$ were added, heating again at 60° C. for 4.5 hours.

Adding HCl 10% (75 mL) +o the reaction mixture, followed by extraction with CH$_2$Cl$_2$ (3×20 mL), the organic phase washed with a saturated Cu-SO$_4$ solution, dried with anhydrous NaSO$_4$ and concentrated at reduced pressure, led to a solid residue, that was purified by chromatography in a silica flash gel column (20×2 cm $\phi$, CH$_2$Cl$_2$ to CH$_2$Cl$_2$:ETOAc gradiet 17:3, yielding after vacuum drying 389 mg of a non-separated mixture of products (XIII) and (XIV).

Spectoscopic data of the mixture:
RF.: 0.36 (CH$_2$C$_2$:EtOAc 7:3).
IR(NaCl, $\gamma_{max}$): 1680, 1720, 1740, 1790, 2960 cm$^{-1}$ UV (Ethanol, $\lambda_{max}$): 204, 224, 266, 338 nm Mass spectrum (m/e, %): 572 (M$^+$, 0.2), 530 (M$^+$, —CH$_2$CO, 3), 514 (M$^+$—CH$_2$OCO, 2), 472 (M$^+$—CH$_2$CO—CH$_2$OCO, 32), 430 (M$^+$—CH$_2$CO—CH$_2$OCO—CHCO—CH$_2$CO—CH$_2$OCO, 100), 317 (M$^+$—CH$_2$CO—CH$_2$—OCO—CH$_3$(C$_6$H$_4$)SO$_2$, 60), 284 (M$^+$—CH$_2$CO—CH$_3$ OCO—CH$_3$(C$_6$H$_4$)SO$_2$—CH$_3$OH, 63), 242 (M$^+$—CH$_2$COCH$_3$OCO—CH$_3$(C$_6$H$_4$)SO$_2$—CH$_2$CO—CH$_3$OH, 58), 139 (CH$_3$(C$_6$H$_4$)SO$_+$, 38) 91 (CH$_3$(C$_6$H$_4$)$^+$, 50). Mass spectrum (FAB) (m/e, %): 573 (M+1.3), 531 (M+1—CH$_2$CO, 23), 515 (M+1—CH$_2$OCO, 24), 501 (M$^*$+1—CH$_2$CO, 7) 488 (M+1—CH$_2$CO—CH$_3$CO, 23), 472 (M+1—CH$_2$CO—CH$_3$OCO, 24), 430(M+1—CH$_2$CO—CH$_2$CO, 100), 400 (M$^*$+1—CH$_2$CO—CH$_3$OCO—CH$_2$CO, 26), 418 (M+1—CH$_3$(C$_6$H$_4$)SO$_2$,10), 399 (M+1—CH$_2$CO—CH$_3$OCO—CH$_2$CO—CH$_3$O, 44), 367 (M+1—CH$_2$CO—CH$_3$OCO—CH$_2$CO—CH$_3$O—CH$_3$OH, 25), 360 (M+1—CH$_2$OCO—CH$_3$(C$_6$H$_4$)SO$_2$, 35), 318 (M+1—CH$_2$OCO—CCH$_3$(C$_6$H$_4$)SO$_2$—CH$_2$CO, 24).

3. Treating the mixture of pyrroloindols (XIII) and (XIV) with sodium and naphthalene.

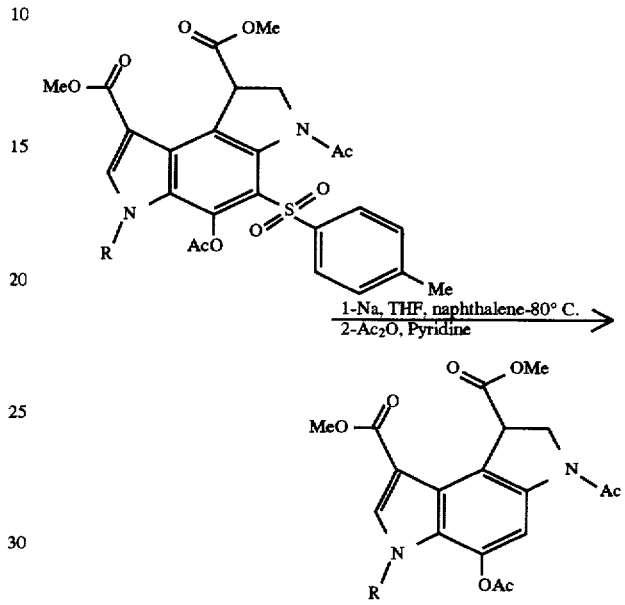

(XIII) R=CH$_2$OCH$_3$ (XV) R=CH$_2$OCH$_3$ Traces (XIV) R=CH$_3$ (XVI) R=CH$_3$ 28% from (XII)

A mixture of naphthalene (320 mg. 2.49 mmol) and sodium (55 mg, 2.39 mmol) in dry THF (10 mL), was maintained with agitation at −15° C. under argon for 2.5 hours. Afterwards the reaction mixture was cooled to −80° C. and the mixture of pyrroloindols (XIII) and (XIV) (105 mg. 0.194 mmol) was added to it, maintaining agitation until the starting substances disappear by TLC (10 minutes), moment in which the acetic anhydride (1 mL, 10.57 mmol) and pyridine (1 mL, 12.39 mmol) are added, passing in turn the reactoin mixture at room temperature and leaving it with agitation and under argon for 24 hours.

Acidifying with HCl 10% (20 mL) of the reaction mixture, followed by extraction with EtOAc (3×10 mL), the organic phase washed with a saturated CuSO$_4$ solution, dried with anhydrous Na$_2$SO$_4$ and purified by chromatography in a silica flash gel column (14×2 cm $\phi$, CH$_2$Cl$_2$:EtOAc gradient from 30 to 40% in EtoAc), yielded 35 mg of a mixture of homogenous products by TLC. This mixture was purified by HPLC (isopropanol:hexanol gradient from 40 to 20% in hexane, flow 3.5 mL/min and detection at 275 nm), separating after vacuum drying, 28 mg. of pyrroloindol (XVI) (28% in two stages, from the compound (XII), along with traces of pyrroloindol (XV).)

Spectroscopic data of pyrroloindol (XVI): m.p.: 223°–224° C. (methanol), Rf.: 0.36 (CH$_2$Cl$_2$:EtOAc 7:3:) IR (NaCl, $\gamma_{max}$) 1655, 1705, 1735, 1765, 2960, 3120 cm UV (Ethanol, $\lambda_{max}$): 214$_{hb}$, 254, 298 nm $^1$H-NMR(CDCl$_3$): 2.20 (s, 3H, RCOCH$_3$), 2.35 (s, 3H, RCOCH$_3$), 2.35 (s, 3H, RCOCH$_3$), 3.63 (s, 3H, ArCH$_3$), 3.76 (s, 3H, ArCH$_3$), 3.76 (s, 3H, ArCO$_2$CH$_3$, 3.84 (s, 3H, ArCo$_2$CH$_3$), 4.31 (m, 2H, RCH$_2$CH(R)$_2$), 5.02 (dd, 1H, J=5.1 and 9.5 Hz, RCH$_2$CH$_R$2), 7.62 (s, 1H, ArH), 8.08 (s, 1H, ArH). $^{13}$C—

NMR(CDCl$_3$): 20.8, 24.0, 36.1, 46.0, 50.9, 52.1, 52.8, 106.7, 107.6, 117.0, 125.7, 126.6, 136.7, 138.4, 139.1, 164.5, 167.9, 169.4, 173.0. Mass spectgrum (m/e, %): 388 (M$^+$, 10), 346 (M$^+$—CH$_2$CO 9) 330 (M$^+$—CO$_2$CH$_2$, 25), 213 (M$^+$—CO$_2$CH$_2$—CH$_2$CO—CH$_3$CO—CH$_3$OH, 51), 197 (M$^+$—CO$_2$CH$_2$—CH$_2$CO—CH$_3$CO—CH$_3$OH—CH$_3$—H, 100). Mass spectrum (high resolution) for C$_{19}$H$_{20}$N$_{20}$N$_2$O$_7$: Calculated: 388.1270; Found: 388.1274.

4. Treating the mixture of pyrroloindols (XIII) and (XIV) with soldium and N,N-dimethyl-1-naphthylamine.

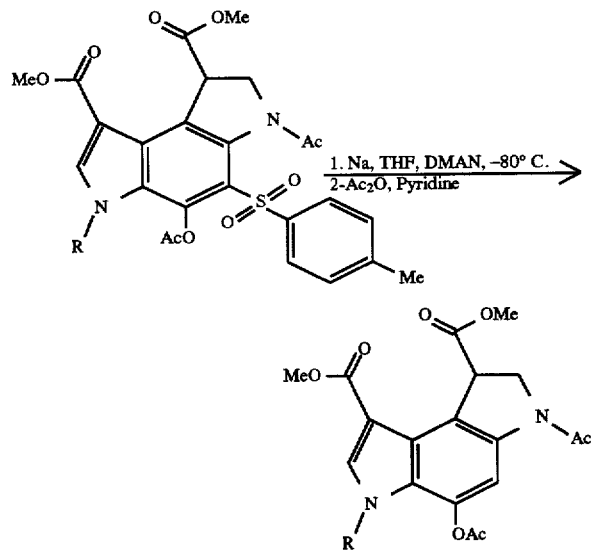

(XIII) R=CH$_2$OCH$_3$ (XV) R=CH$_2$OCH$_3$ Traces (XIV) R=CH$_3$ (XVI) R=CH$_3$ 26% from (XII)

A mixture of N,N-dimethyl-1-naphthylamine (0.3, mL, 1.827 mmol) and sodium (25 mg, 1.087 mmol) in dry THF (5 mL) was kept with agitation under argon in a bath at −15° C. for 1.5 hours. Then the reaction mixture was cooled at −80° C. and the mixture of the compounds (XIII) and (XIV) was added to it, maintaining agitation in the bath for 20 minutes. To the reaction mixture at this temperature 0.8 ml of acetic anhydride (8.46 mmol) and 0.5 mL of pyridine (6.19 mmol) were then added, passing the mixture at room temperature and maintaining the reaction for 40 hours.

Adding HCl 10% (10 mL) to the reaction mixture, followed by extraction with EtOAc (3×4 mL), the organic phase washed with a saturated CuSO$_4$ solution, dried with anhydrous Na$_2$SO$_4$ and purified by chromatography in a silica flash gel column (15×1.5 cm φ, EtOAc:hexane gradient from 10 to 0% in hexane), provided 33 mg of a mixture which after purification HPLC (isopropanol:hexane gradient from 40 to 20/ in hexane, flow 3.5 mL/min and detection at 275 nm) yielded after vaccum drying 26 mg of the pyrroloindol (XVI) (26% in two stages, from compound (XII), along with traces of the pyrroloindol (XV).

5. Synthesis of methyl 6-acetyl-8-hydroxymethyl-4-ol-3-methyl-3,6,7,8-tetrahydropyrrolo[3,2-e]indol-1-carboxylate

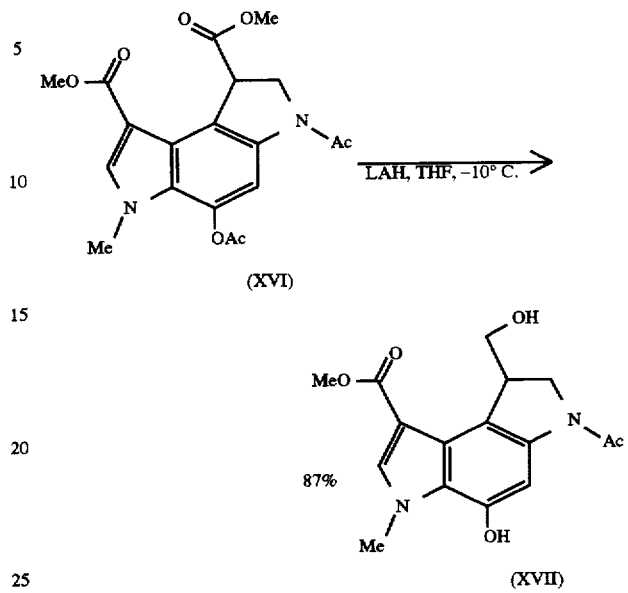

0.32 mL of a solution of LiAlH$_4$ in THF (1M, 0.32 mmol) was added to a solution agitated under argon and cooled to −10° C. of pyrroloindol (XVII) (42 mg. 0.108 mmol) in dry THF, maintaining the agitation at a low temperature for 30 minutes.

Adding EtOAc (2 ml) to the reaction mixture, followed by acidifying with HCl 10%, adding a saturated NaCl solution (5 ml), extracting with EtOAc (5×4 mL), drying with anhydrous Na$_2$SO$_4$ and eliminating the solvent, yielded a solid residue that was passed through a slica flash gel column (18×1 cm φ), eluting with EtOAc:methanol (9:1), yielding 30 mg (87%) of the diol (XVII). m.p.: 201°–205° C. (dry) (EtOAc). Rf.: 0.20 (EtOAc). IR (KNr, γ$_{max}$) 1610, 1636m 1674m 1702, 3121, 3434 cm$^{-1}$ UV (Ethanol, λ$_{max}$): 254, 312 nm.) $^1$H—NMR(DMSO—D$_6$): 2.15 (s, 3H, ArCOCH$_3$), 3.00 (m, 1H, R$_2$CHR), 3.67 (m, 1H, RCH$_2$NR$_2$), 3.73 (s, 3H, ARCH$_3$), 4.00 (s+m, 5H, ArCO$_2$CH$_3$ and RCH$_2$OH), 4.12 (m, 1H, RCH$_2$NR$_2$), 4.70 (s wide, 1H, RCH$_2$OH), 7.75 (s, 1H, ArH), 7.91 (s, 1H, ArH), 10.00 (s wide, 1H, ArOH). Mass spectrum (m/e, %): 318 (M$^+$, 31), 300 (M$^+$—H$_2$O, 5), 287 (M$^+$—HOCH$_2$, 74), 255 (M$^+$—HOCH$_2$—CH$_2$—CH$_3$OH, 21), 228 ((M$^+$—HOCH$_2$—CO$_2$CH$_3$, 8) 213 (M$^+$—HOCH$_2$—CH$_2$CO—CH$_3$OH, 100) 186 (M$^{30}$—HOCH$_2$CO$_2$CH$_3$—CH$_2$CO, 19). Mass spectrum (high resolution for C$_{16}$H$_{18}$N$_2$O$_3$: Calculated: 318.1216; Found: 318.1223

6. Synthesis of methyl 2-acetyl-5-methyl-4-oxo-1,2,4,5,8,8a-hexahydrocyclopropa[c]pyrrolo[3,2-e]indol-7-carboxylate (VII)

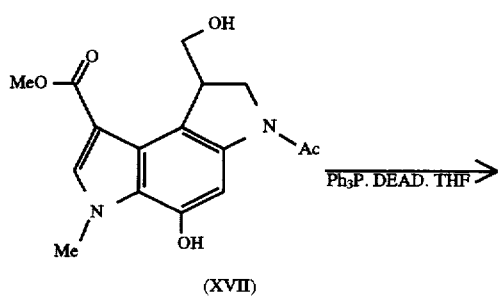

(XVII)

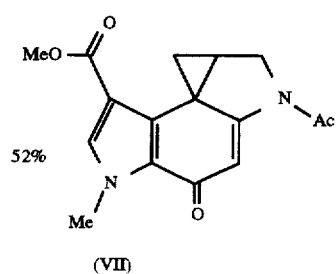

(VII)

0.03 mL of diethyl azodicarboxylate (0.189 mmnol) were added to a magnetically agitated solution under argon of the diol (XVII) (27 mg. 0.085 mmol) and triphenylphosphine (74 mg. 0.282 mmol) in dry THF, maintaining agitation for 19 hours.

After purifying by chromatography in a silica flash gel column (18×1 cm φ) elutinig with EtOAc:hexane (17:3, of the residue obtained by eliminating the solvent at reduced pressure, 105 mg of a triphenylphosphine oxide and reaction product mixture were isolated. Finally, by purifying this mixture by HPLC (isopropanol:hexane gradient from 35 to 20% in hexane, flow 3.5 mL/min and detection at 254 nm) 13 mg (52%) of the analogue (VII) of the fragment (CPI) were isolated. m.p.: 193°–195° C. (CH$_2$Cl$_2$:hexane). RF.:

0.41 (EtOAc). IR(KBr): 1595, 1616, 1688, 2948 cm$^{-1}$ UV (Ethanol, $\lambda_{max}$): 220, 244, 280, 294 330 nm $^1$H—NMR (CD$_2$Cl$_2$): 1.19 (m, 1H, RCH$_2$R), 2.17 (s+m, 4H, ArCOCH$_3$ and RCH$_2$R), 3.49 (m, 1H, R$_2$CHR), 3.72 (s, 3H, ArCH$_3$), 4.00 (s+m, 5H, ArCO$_2$CH$_3$ and RCH$_2$NR$_2$), 6.83 (s, wide; 1H, RCOCHR), 7.36 (s, 1H, ArH). $^{13}$C—NMR(CDCl$_3$), 23.9, 24.3, 24.5, 32.2, 37.1, 51.1, 53.2, 108.9, 111.5, 129.6, 132.0, 134.2, 159.5, 163.8, 170.0, 178.5. Mass spectrum (m/e, %): 300 (M$^+$, 26), 269 (M$^+$—CH$_3$O,3), 257 (M$^+$—CH$_3$CO, 40), 243 (M$^+$—CH$_3$CO—CH$_2$, 22), 225 (M$^+$—CH$_3$CO—CH OH, 19), 198 (M$^+$—CH$_3$CO—CH$_3$OCO, 19), 43(CH$_3$CO$^+$, 100). Mass spectrum (high resolution) for C$_{16}$H$_{16}$N$_2$O$_4$: Calculated: 300.1110; Found: 300.1097.

EXAMPLES OF SYNTHESIS

Example 1

Synthesis of methyl 8,chloromethyl-4-hydroxy-3-methyl-3,6,7,8-tetrahydropyrrolo[3,2-e]indol-1-carboxylate hydrochloride (IX)

(a) Synthesis of methyl 5-methyl-4-oxo-1,2,4,5,8,8a-hexahydrocyclopropa[c]pyrrolo[3,2-e]indol-7-carboxylate (VII).

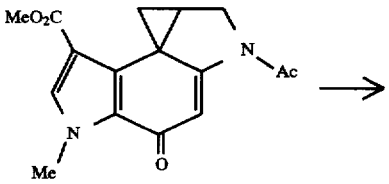

(VII)

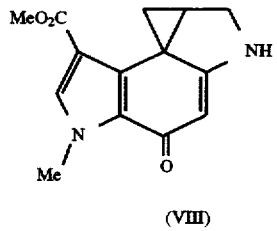

(VIII)

0.2 mL of a 1.25M sodium methoxide solution in methanol were added to a solution agitated magnetically under argon of the compound (VII) (13 mg. 0.043 mmol) in dry methanol (4 mL). maintaining the agitation at room temperature for 10 minutes.

After purifying in a silica flash gel column (10×1 cm φ). the residue obtained by eliminating the solution under reduced pressure, eluting with EtOAC, 11 mg (99%) of the compound (VIII) were isolated. RF.: 0.26 (EtOAc). $^1$H-NMR(CD$_2$Cl$_2$): 1.11 (dd, 1H, J=2.9 and 4.8 Hz, RCH$_2$R), 2.04 (dd, 1H, J=2.8 and 7.8 Hz, RCH$_2$R),3.48 (m, 1H, R$_2$CHR), 3.54 (d 1H, J=10.2 Hz, RCH$_2$R), 3.71 (m+s, 4H, RCH$_2$R and ArCH$_3$), 3.98 (s, 3H, ArCO$_2$CH$_3$), 5.18 (s wide, 1H, NH), 5.37 (s, 1H, RCOCHR), 7.25 (s, 1H, ArH). Mass spectrum (m/e, %): 258 (M$_+$, 100), 243 (M$^+$—CH$_3$, 17), 225 (M$^+$—CH$_3$OH—H, 32), 199 (M$^+$—CO$_2$CH$_3$, 40).

(b) Synthesis of methyl 8-chloromethyl-4-hydroxy-3-methyl-3,6,7,8-tetrahydropyrrolo[3,2-e]indol-1-carboxylate hydrochloride (IX).

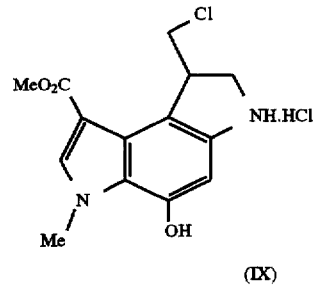

(IX)

For 30 minutes, the anhydrous hydrogen chloride was bubbled through a solution of compound (VIII) (11 mg., 0.042 mmol) in dry ethyl acetate (3mL), keeping the reaction at room temperature.

The resulting yellow suspension was concentrated at reduced pressure and vacuum dried, permitting the isolation of 13 mg (93%) of compound (IX.)

Example 2

Synthesis of methyl 6-{5-[(benzofuran-2-ylcarbonyl)-amino]1H-indol-2-carbonyl}-8-chloromethyl-4-hydroxy-3-methyl-3,6,7,8,tetrahydropyrrolo[3,2-e]indol-1-carboxylate (III)

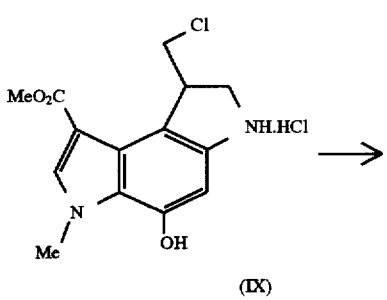

(IX)

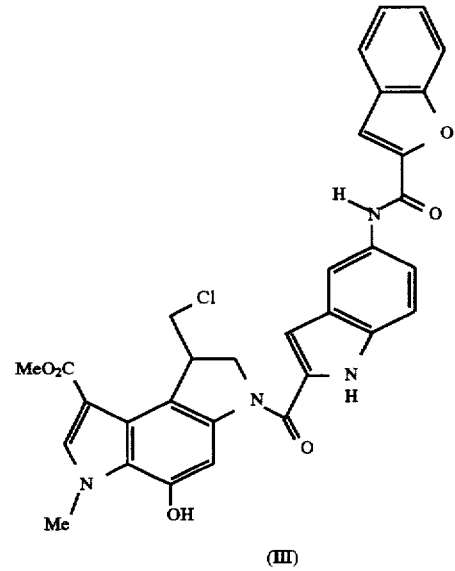

(III)

A mixture of the compound (IX) (21 mg., 0.063 mmol), of 5-(benzofuran-2-ylcarbonyl)amino -1H-indol-2-carboxylic acid (84 mg, 0262 mmol) and N-(3,3-dimethylaminopropyl)-N-ethylcarbodiimde hydrochloride (79 mg, 0.412 mmol) in dry DMF (2 mL), was maintained with agitation at room temperature and under argon for 24 hours.

Adding water (5 mL) and brine (2 mL) to the reaction mixture, followed by extracting with EtOAc (4×5 mL), the organic phase dried with anhydrous $Na_2SO_4$ and purifying by chromatography in a slica flash gel column (14×1.5 cm ϕ) eluting with EtOAc:Hexane (17:3), made it possible to obtain after vacuum drying, 26 mg. (69%) of compound (III).

Rf.: 0.60 (Hexane:acetone 1:1) 1H:NMR (Acetone-$D_6$:DMSO—$D_6$ 9:1): 3.49 (dd, 1H, J 8.9 and 10.3 Hz, $R_2CHCH_2NR_2$), 3.81 (s, 3H, $ArCH_3$), 3.99 (dd, 1H, J=3.1 and 10.3 Hz, $R_2CHCH_2NR_2$), 4.12 (s, 3H, $ArCO_2CH_3$), 4.48 (m, 1H, $R_2$CHCH2Cl), 4.67 (m, 2 H, $R_2CHCH_2Cl$), 7.19 (d, 1H, J=1.6 Hz, ArH), 7.35 (dt, 1H, J=1.0 and 7.45 Hz, ArH), 7.51 (m, 2H, ArH), 7.68 (m, 3H, ArH), 7.81 (dd, 1H, J=1.0 and 7.5 Hz, ArH), 7.92 (s, 1H, ArH), 7.95 (s, 1H, ArH), 8.34 (d, 1H, J=1.7 Hz, ArH), 10.06 (s, 1H, ArOH), 10.21 (s, 1H, ArNHCOAr), 10.24 (s, wide, 1H, ArNH).

Example 3

Synthesis of methyl 2-[5-[(benzofuran-2-ylcarbonyl)amino]-1H-indol-2-carbonyl]-5-methyl-4-oxo,1,2,4,5,8,8,a-hexahydrocyclopropa[c]pyrrolo[3,2-e]indol-7-carboxylate (IV).

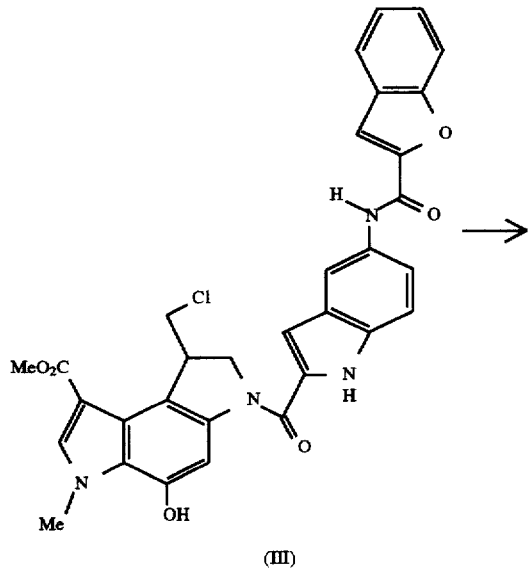

(III)

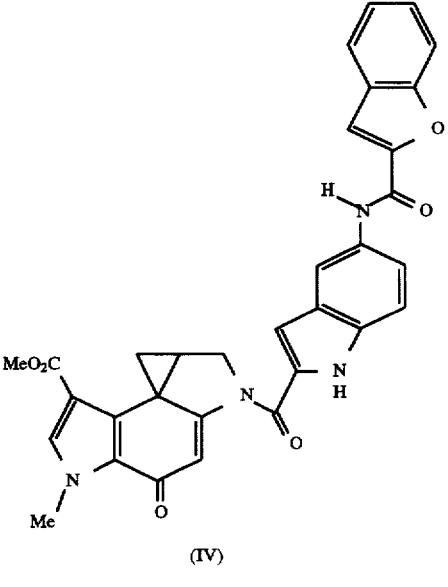

(IV)

Compound (III) was dissolved in 3.5 ml of a mixture of acetonitrile:water:triethylamine (5:1:1), maintaining agitation at room temperature for 1 hour.

The resulting solution was diluted in EtOAc (50 mL), washed with water (3×15 mL), dried with anhydrous $Na_2SO_4$ and purified by chromatography in a silica flash gel column (9×1, cm ϕ), eluting with acetone:hexane (1:1). After vacuum drying 8 mg. (95%) of compound (IV) were obtained.

Rf.: 0.55 (Acetone:hexane 3:2). 1H:NMR ($CD_2Cl_2$:DMSO—$D_6$ 9:1): 1.26 (m 1H, $RCH_2CHR_2$), 2.14 (dd, 1H, J=3.2 and 7.5 Hz, $RCH_2CHR_2$), 3.57 (m, 1H, $RCH_2CHR_2$) 3.65 (s, 3H, $ArCH_3$), 3.93 (s, 3H, $ArCO_2CH_3$), 4.35 (m, 2H, $RCH_2NR_2$), 6.77 (s, 1H, ArH), 6.93 (s, 1H, ArH), 7.22 (t, 1H, J=7.6 Hz, ArH), 7.37 (m, 2H, ArH), 7.49 (m, 2H, ArH), 7.63 (d, 1H, J=7.8 Hz, ArH), 8.11 (s, 1H, ArH), 9.66 (s, 1H, ArNHCOAr), 11.35 (s, 1H, ArNH).

Example 4

Synthesis of methyl 6-(5,6,7-trimethoxy-1H-indol-2-carbonyl)-8-chloromethyl-4-hydroxy-3-methyl-3,6,7,8-tetra-hydropyrrololo[3,2-e]indol-1-carboxylate (V).

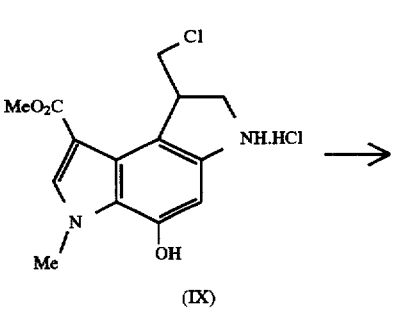

(IX)

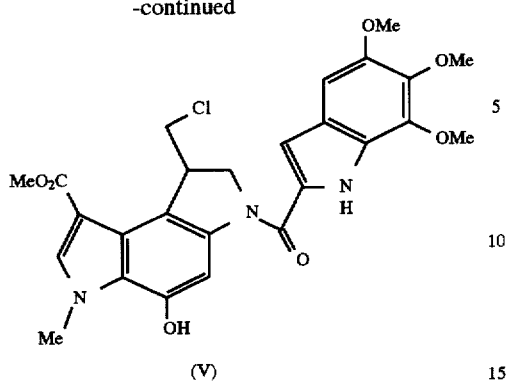

(V)

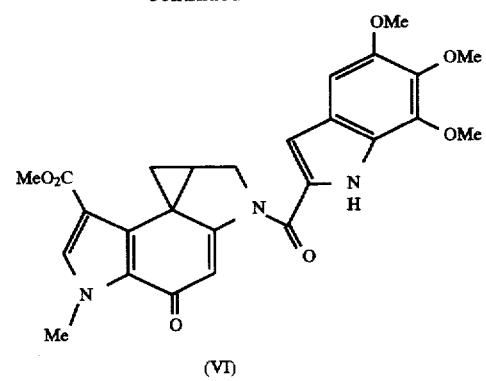

(VI)

A mixture of compound (IX) (13 mg, 0.039 mmol), 5,6,7-trimethoxy-1H-indol-2-carboxylic acid (35 mg., 0.144 mmol) and N-(3,3-dimethylaminopropyl)-N-ethylcarbodiimide hydrochloride (46 mg, 0.24 mmol) in dry DMF (1.5 mL), was maintained with agitation at room temperature and under argon for 24 hours.

Adding water (5 mL) and brine (2 mL) to the reaction mixture, followed by extracting with EtOAc (4×5 mL), the organic phase dried with anhydrous $Na_2SO_4$ and purifying by chromatography in a silica flash gel column (13×1 cm φ) eluting with EtOAc:hexane (17:3), made it possible to obtain after vacuum drying, 18 mg (87%) of compound (V).

Rf.: 0.65 (Hexane:acetone 1:1) $^1$H-NMR (Acetone-$D_6$): 3.46 (m, 1H, $R_2$CHCH$_2$NR$_2$, 3.80 (s, 3H, RCH$_3$), 3.85 (s, 3H, RCH$_3$) 3.86 (s, 3H, RCH$_3$), 3.98–4.00 (m, 1H, R2CHCH$_2$NR$_2$), 4.01 (s, 3H, RCH$_3$) 4.13 (s, 3H, RCH$_3$), 4.58 (m, 3H, $R_2$CHCH$_2$Cl and $R_2$CHCH$_2$Cl), 6.96 (s, 1H, ArH), 7.08 (d, 1H, J=2.2 Hz, ArH), 7.86 (s, 1H, ArH), 7.94 (s, 1H, ArH), 9.22 (s wide, 1H, ArNH), 10.28 (s, wide, 1H, ArOH).

Example 5

Synthesis of methyl 2-(5,6,7-trimethoxy-1H-indolz2-carbonyl)-5-methyl-4-oxo-1,2,4,5,8a-hexahydrocyclopropa[c]pyrrolo[3,2-e]indol-7-carboxylate (VI)

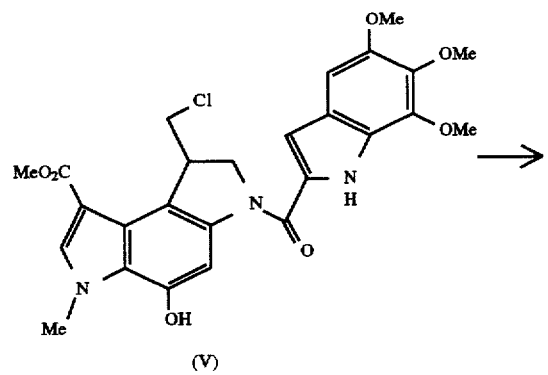

(V) →

Compound (V) was dissolved in 2.5 mL of a mixture of aceto-nitrile:water:triethylamine (3:1:1), maintaining the agitation at room temperature for 1 hour.

The resulting solution was diluted with EtOAc (50 mL), washed with water (3×15 mL), dried with anhydrous $Na_2SO_4$ and purified by chromatography in a silica flash gel column (12×1 cm φ), eluting with EtOAc:hexane (4:1). After vacuum drying 13 mg. (83%) of compound (VI) were obtained. Rf.: 0.45 (Acetone:hexane 1:1). $^1$H—NMR (CD$_2$Cl$_2$): 1.32 (1H, RCH$_2$CHR$_2$), 2.24 (dd, 1H, J=3.5 and 7.6 Hz, RCH$_2$CHR$_2$), 3.61 (m, 1H, RCH$_2$CHR$_2$), 3.75 (s, 3H, RCH$_3$), 4.02 (s, 3H, RCH$_3$), 4.03 (s, 3H, RCH$_3$), 4.034 (s, 3H, RCH$_3$), 4.40 (d, 2H, J=2.6 Hz, RCH$_2$NR$_2$), 6.82 (s, 1H, ArH), 6.91 (s, 1H, ArH), 6.93 (d, 1H, J=2.3 Hz, ArH), 7.39 (s, 1H, ArH), 9.34 (s wide, 1H, ArNH).

Example 6

Synthesis of methyl 4-acetoxy-6-{5-[(benzofuran-2-yl-carbonyl)-amino]1H-indol-2-carbonyl-}8-chloromethyl-3-methyl-3,6,7,8-tetrahydropyrrolo[3,2-e]indol-1-carboxylate (IIIa)

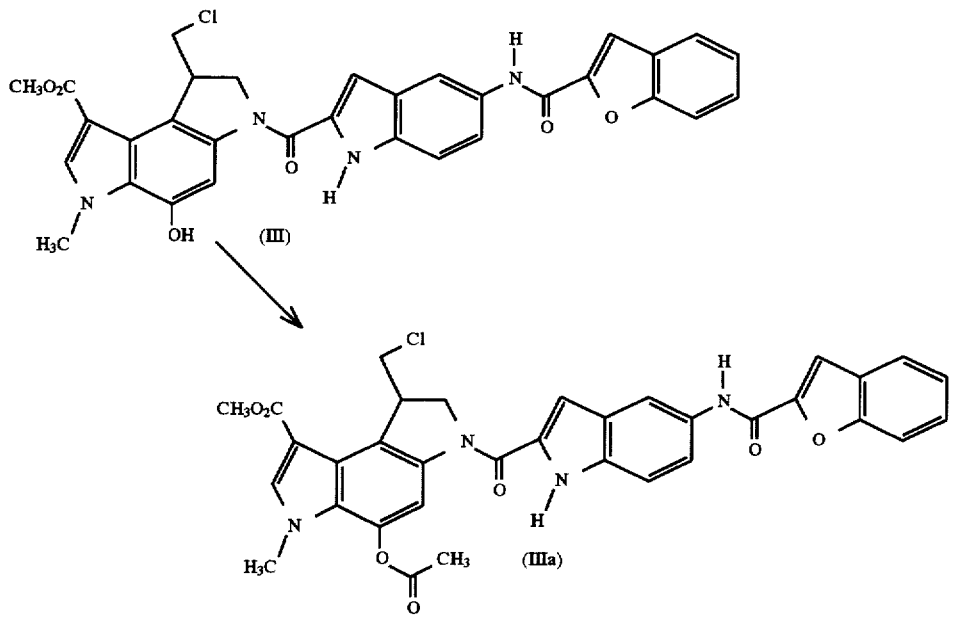

A solution of acetyl chloride (0.024 mL, 0.034 mmol) in dry tetrahydrofuran (2 mL) was added to a solution, cooled to −20° C. and agitated under argon of compound (I) (10 mg, 0.017 mmol) and triethylamine (0.047 mL, 0.34 m mmol) in dry tetrahydrofuran (3 mL).

Half an hour later the resulting solution was passed at room temperature and brine (2 mL) and hydrchloric acid (10%) (2 mL) were added. The solution resulting from extraction with ethyl acetate (3×8 mL) was dried ($Na_2SO_4$) and concentrated, yielding a residue that was purified by chromatography in a silica flash gel (12×1.5 cm φ), eluting with $CH_2Cl_2$:EtOAc (4:1.) 9 mg. (83% of compound (IIIa) were obtained. m.p.: 189°–191° C. (EtOAc). R.f.: 0.60 (hexane:acetone, 1:1). $^1$H—NMR(DMSO—$D_6$): 2.42 (s, 3H, $CH_3CO$), 3.65 (dd, 1H, J=8.2 and 10.7 Hz, $R_2CHCH_2NR_2$), 3.80 (s, 3H, $ArCH_3$), 3.92 (s, 3H, $ArCO_2CH_3$), 3.97 (m, 1H, $R_2CHCH_2NR_2$), 4.50 (m, 1H, $R_2CHCH_2Cl$), 4.62 (d, 1H, J=10.7 Hz, $R_2CHCH_2Cl$), 4.76 (m, 1H, $R_2CHCH_2Cl$), 7.19 (s, 1H, ArH), 7.36 (t, 1H, J=7.8 Hz, ArH), 7.48 (d, 1H, J=8.8 Hz, ArH), 7.50 (m, 1H, ArH), 7.60 (dd, 1H, J=1.0 and 8.0 Hz, ArH); 7.72 (d, 1H, J=8.1 Hz, ArH), 7.75 (s, 1H, ArH), 7.82 (d, 1H, J=7.8 Hz, ArH), 8.02 (s, 1H, ArH), 8.18 (s, 1H, ArH), 8.19 (s, 1H, ArH), 10.45 (s, 1H, ArNHCOAr), 11.67 (s, 1H, ArNH).

Example 7

Synthesis of methyl 6-{5-[(benzofuran-2-ylcarbonyl)-amino 1H-indol-2-carbonyl}-8-chloromethyl-3-methyl-4-(4-nitrobenzolyl)-3,6,7,8-tetrahydropyrrolo[3,2-e]indol-1-carboxylate (IIIb)

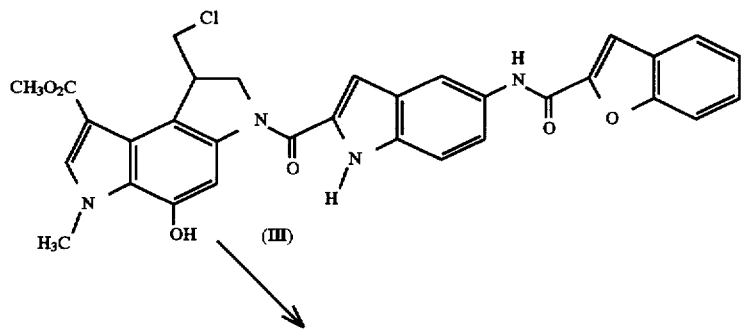

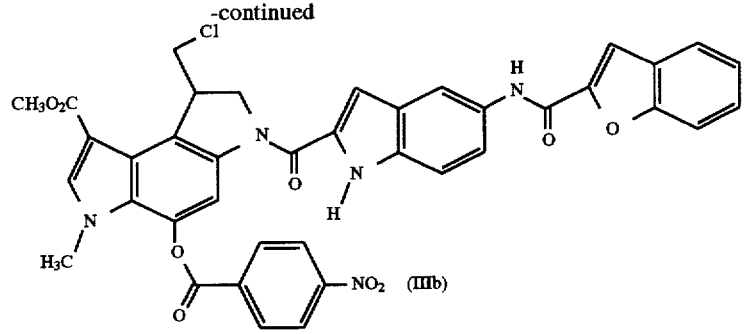

A solution of compound (I) (15 mg. 0.025 mmol), 4-nitrobenzoic acid (34 mg. 0.020 mmol) and N-z(3,3-dimethylaminopropyl)-N-ethylcarbodiimide hydrochloride (43 mg. 0.22 mmol) in dry dimethylformamide (1 mL) was kept at room temperature with agitation under argon for 20 hours.

The mixture resulting from adding brine (3 mL) and hydrochloric acid (10%) (3 mL) was extracted with ethyl acetate (3×8 mL). The organic phase was washed with an aqueous saturated sodium bicarbonate solution (4 mL) and dried over anhydrous sodium sulfate. After concentrating a residue that was purified by chromatography in a silica flash gel column (12×1.5 cm φ) was obtained, eluting with $CH_2Cl_2$:EtOAc (4:1), yielding 15 mg (80%) of compound (IIIb). m.p.: 260° C. (dry, $CH_2Cl_2$), Rf.: 0.65 (hexane:acetone, 1:1). $^1H$—NMR($Cl_3CD$): 3.50 (dd, 1H, J=9.3 and 9.7 Hz, $R_2CHCH_2NR_2$), 3.86 (s, 3H, $ArCH_3$), 3.92 (s, 3H, $ArCO_2CH_3$), 4.00 (dd, 1H, J=11.0 and 13.7 Hz $R_2CHCH_2NR_2$), 4.65 (m, 1H, $R_2CHCH_2$ Cl), 4.71 (m, 1H, $R_2CHCH_2Cl$), 4.87 (d, 1H, J=9.6 Hz, $R_2CHCH_2Cl$), 7.12 (s, 1H, ArH), 7.33 (t, 1H, J=7.6 Hz, ArH), 7.47 (m, 3H, ArH), 7.58 (d, 1H, J=8.3 Hz, ArH), 7.61 (s, 1H, ArH), 7.72 (d, 1H, J=7.6 Hz, ArH), 7.76 (s, 1H, ArH), 8.26 (s, 1H, ArH), 8.31 (s, 1H, ArH), 8.40 (s, 1H, ArNHCOAr), 8.44 (m, 4H, $O_2NArH$), 9.36 (s, 1H, ArNH).

EXAMPLE OF BIOLOGICAL TESTS

BIOLOGICAL ACTIVITY OF THE COMPOUNDS OF THE INVENTION

Description of the P388 Antitumoral Model

The original tumoral line was chemically induced in 1955 in a DBA/2 mouse painting its skin with 3-methylcholanthrene. Normally, $1×10^6$ cells in ascitic fluid was implanted, i.p. in $CD_2F_1$ mice. Treatment with the agent tested i.p. began one day after the tumor had been implanted and it is continued daily up to a total of 5 injections for synthetic products and of 9 injections for raw natural products. The results are expressed as percentage of the control survival time.

Procedure

CDF1 mice weighing 18–22 gr (+/−3 gr) were implanted on day 0 of the test period 0.1 ml. of a dilution of $1.0×10^7$ tumor cells coming from DBA/2N mice used for the propagation of the tumor.

On day 1 of the test period the animals were grouped at randam in groups of six animals. Each group is weighed and the average weight is written down. Each compound to be tested in duluted in 4 lvels of dosis for each multidose test as of the determiantion of the highest non-toxic dose (v.g. 400 mg/kg; 100 mg/kg; 10 mg/kg.)

Administration of the test compounds is started on day 1 using volumns of ½ drug injected i.p. Injections are given on days 1 to 9 of the test period, unless it is indicated to the contrary. The animals are weighed on day 5, which is the one which in this system is considered the day of toxicity. Toxicity in this test system is defined as:

A. 34% deaths up to day 5—acute toxicity

B. C/T <85% —chronic toxicity

C. A negative average of the weight change of the animals >4 g up to day 5—chronic toxicity The data obtained upon testing the compounds in vivo in comparison with the P388 leukemic tumor model in mice are shown in the following table:

| Compound | Inject. dose (mg/kg) | Way | %C/T |
|---|---|---|---|
| (IV) | 0.300 | i.p. | 251.1** |
| (III) | 0.500 | i.p. | >391.3 |
| (VI) | 0.500 | i.p. | 210.9** |
| (V) | 0.050 | i.p. | 133.9** |

Where %C/T means average survival of the tested group/average survival of the controls and untreated ones.
*Significant activity (moderate): C/T > = 125%
**Significant activity (strong): C/T > = 175%

On the other hand, the results of the tests in vitro carried out on compounds (IIIa) and (IIIb) were the following:

| | $IC_{50}$ (μg/mL) | | | |
|---|---|---|---|---|
| COMPOUND | P-388 | A-549 | HT-29 | MEL-28 |
| IIIa | 0.00001 | 0.00005 | 0.00025 | 0.00025 |
| IIIb | 0.00002 | 0.0001 | 0.0005 | 0.0005 |

We claim:

1. Pyrrolo[3,2-e]indole derivatives, characterized in that they have the following formulae (I) (Ia) and (II):

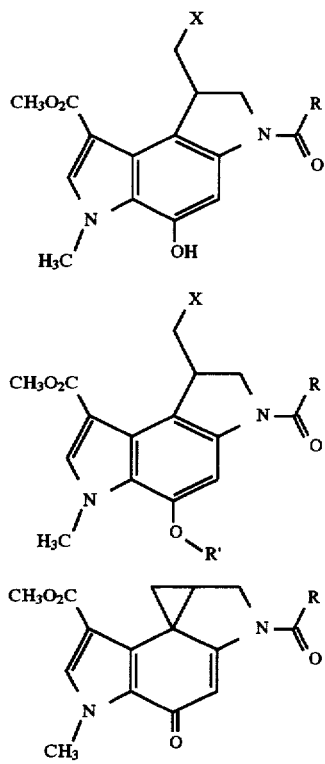

wherein R represents an aryl or heteroaryl group, substituted or not substituted, R' represents alkanoyl, alkenoyl, alkynoyl, arenocarbonyl or heteroarenocarbonyl, substituted or not substituted and X represents chlorine, bromine, iodine or alkyl or arylsulfonyl.

2. A pyrrolo[3,2-e] derivatives, according to claim 1, characterized in that R represents an indolyl group or an indolyl group substituted with an aryl or an heteroarylcarbonylamino group.

3. A pyrrolo[3,2-e]indol derivative, according to claim 1, characterized in that it has the following formulae (III):

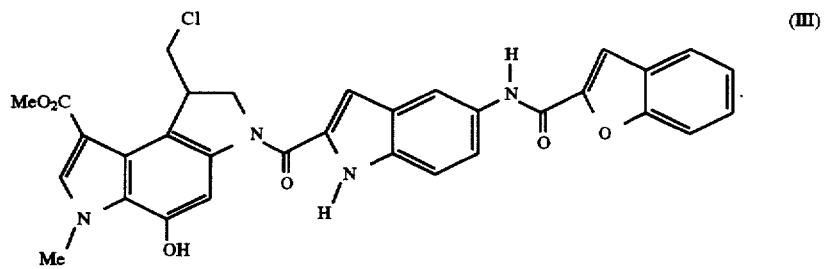

4. A pyrrolo[3,2-e]indol derivative, according to claim 1, characterized in that it has the following formula (IV):

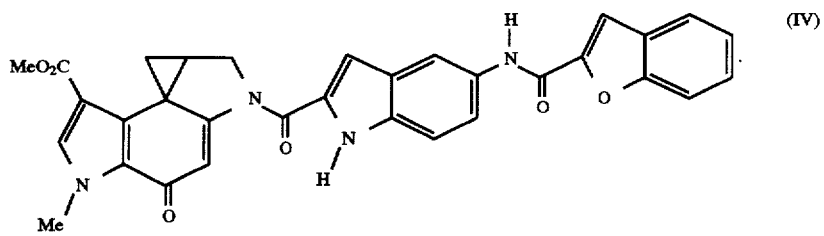

5. A pyrrolo[3,2-e]indol derivative, according to claim 1, characterized in that it has the following formula (V):

6. A pyrrolo[3,2-e]indol derivative, according to claim 1, characterized in that it has the following formula (VI):

7. A pyrrolo[3,2-e]indol derivative, according to claim 1, characterized in that it has the following formula (IIIa):

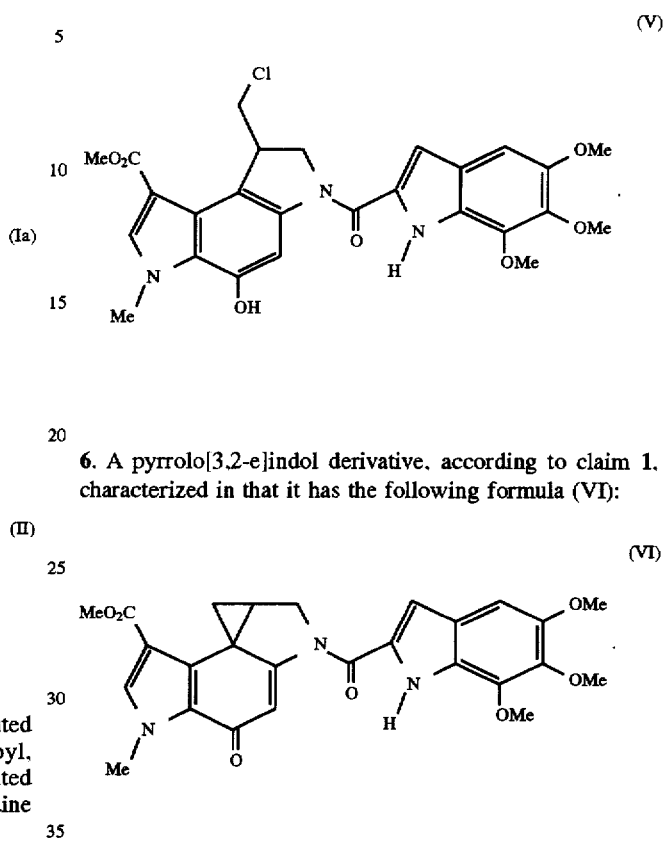

(IIIa)

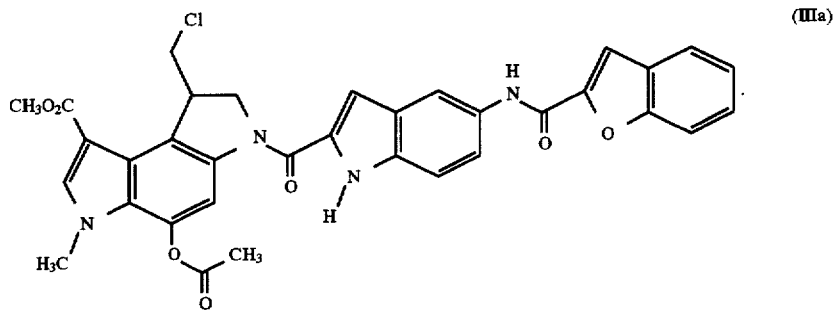

8. A pyrrolo[3,2-e]indol derivative, according to claim 1, chracterized in that it has the following formula (IIIb):

(IIIb)

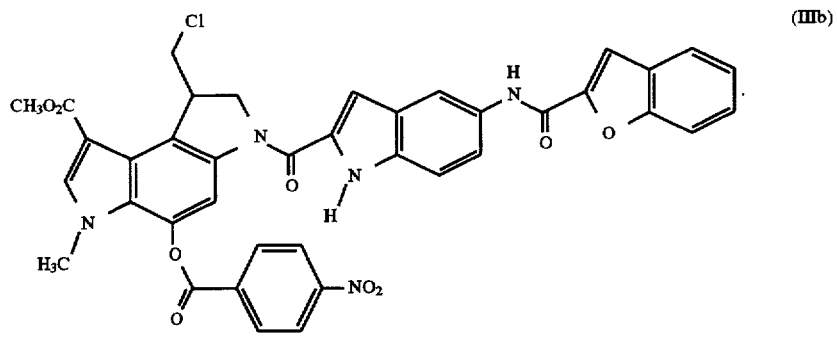

9. A process for the preparation of pyrrolo[3,2-e]indol derivatives, of general formulae (I), (Ia) and (II):

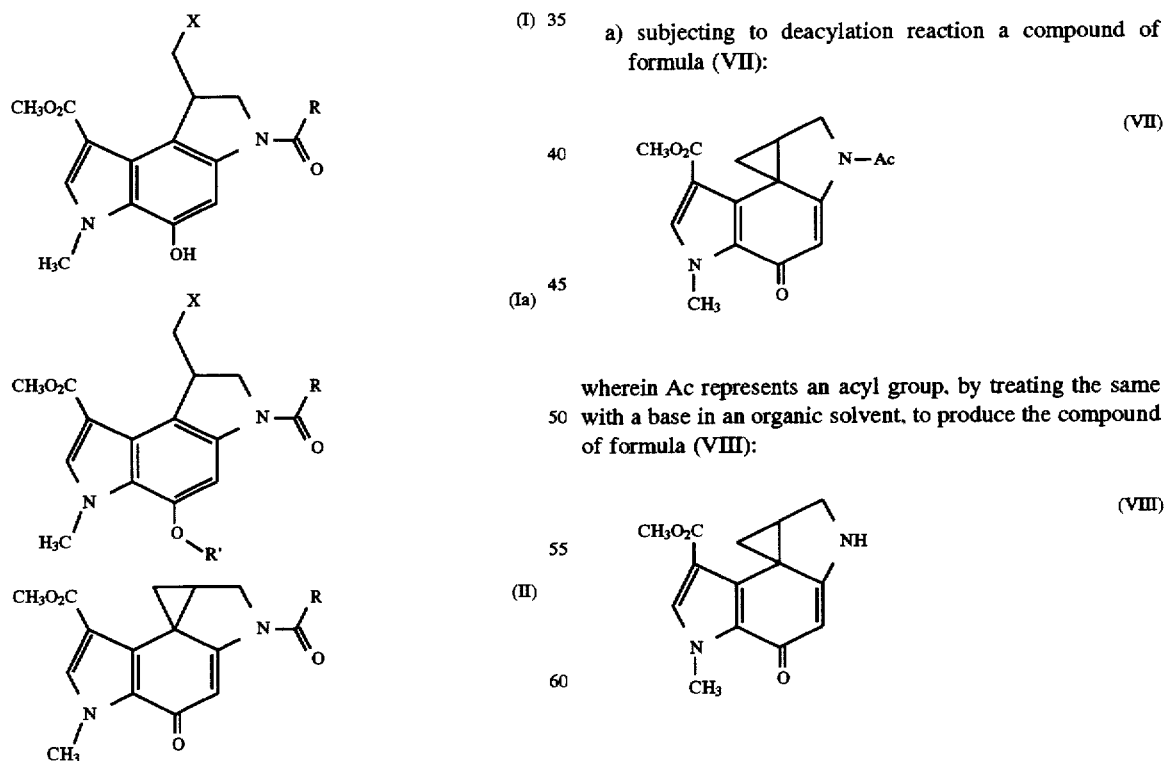

wherein R represents aryl or heteroaryl, substituted or not substited, R' represents alkanoyl, alkenoyl, alkynoyl arenocarbonyl or heteroarenocarbonyl, substituted or not substituted and X represents chlorine, bromine, iodine or alkyl-or arylsulfonyl; whose process is characterized in that it comprises the following steps:

a) subjecting to deacylation reaction a compound of formula (VII):

wherein Ac represents an acyl group, by treating the same with a base in an organic solvent, to produce the compound of formula (VIII):

b) subjecting the compind (VIII) thus obtained to a reaction to open the cyclopropyl ring, by means of treating the same with an acid in an organic solvent, to produce the compound of formula (IX):

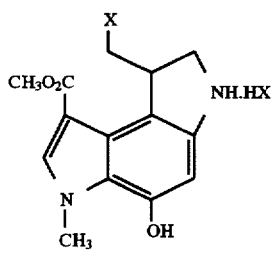

wherin X has the meaning given above for formula (I);

c) subjecting the compound (IX) thus obtained to a condensation reaction with an acid of formula

R—COOH  (X)

wherein R has the meaning given above, or a reactive derivative of the same, to produce the active compound of formula (I) indicated above, carrying out said condensation in an organic solvent and in the presence of a condensing agent;

d) when necessary, treating the compounds of formula (I) thus obtained with a base in a suitable solvent to produce the compounds of formula (II);

e) when necessary, treating the compounds of formula (I), obtained according to step c) alternatively with: (a) a carboxylic acid in-the presence of a condensing agent; or else (b) carboxylic acid chloride in the presence of a base, or both alternatives in a suitable solvent; to produce the compounds of formula (Ia.).

10. A method of using the compounds of formula (I), (Ia) and (II):

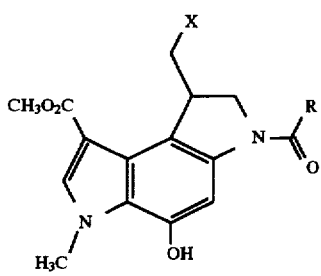

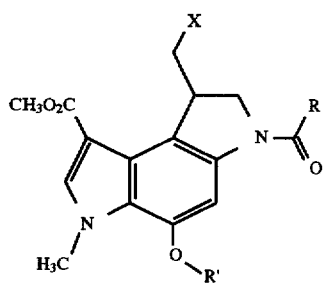

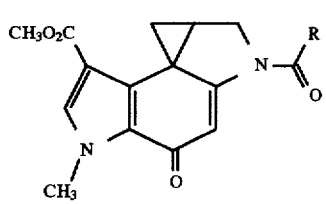

wherein R represents aryl or heteroaryl, substituted or not substituted, R' represents alkanoyl, alkenoyl, alkynoyl, arenocarbonyl or heteroarenocarbonyl, substituted or not substituted and X represents chlorine, bromine, ioodine or alkyl- or arylsulfonyl, as agents having antitumoral activity for the treatment of cancer.

11. The method of use, according to claim 10, of the compound of formula (III):

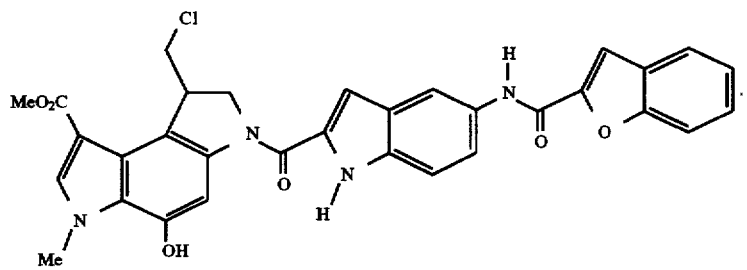

as an agent having antitumoral activity for the treatment of cancer.

12. The method of use, according to claim 10, of the compound of formula (IV):

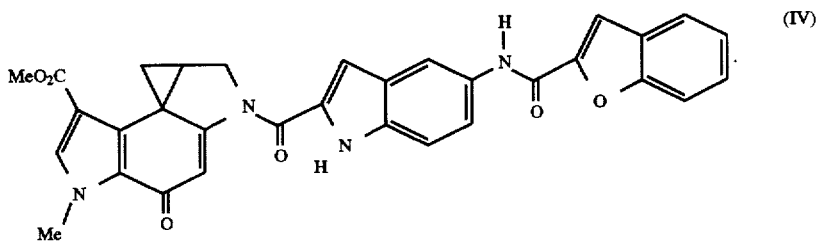

as an agent having antitumoral activity for the treatment of cancer.

13. The method of use, according to claim 10, of the compound of formula (V):

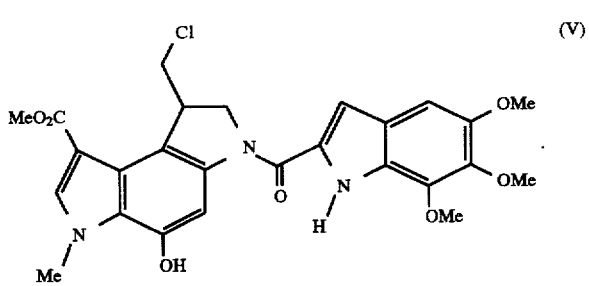

as an agent having antitumoral activity for the treatment of cancer.

14. The method of use, according to claim 10, of the compound of formula (IV):

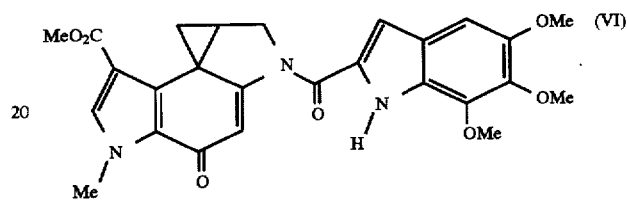

as an agent having antitumoral activity for the treatment of cancer.

15. The method of use, according to claim 10, of the compound of formula (IIIa):

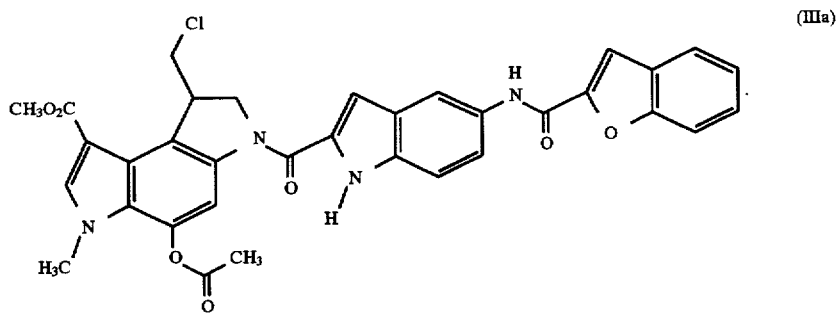

as an agent having antitumoral activity for the treatment of cancer.

16. The method of use, according to claim 10, of the compound of formula (IIIb):

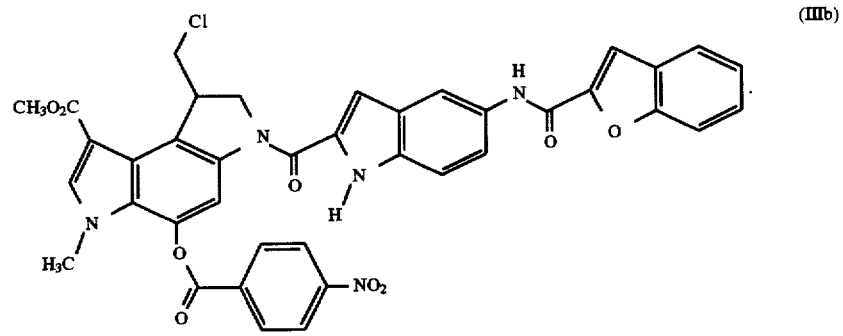

as an agent having antitumoral activity for the treatment of cancer.

* * * * *